United States Patent [19]

Broussard et al.

[11] Patent Number: 5,229,442
[45] Date of Patent: Jul. 20, 1993

[54] STABILIZING COMPOSITIONS FOR ORGANIC POLYMERS

[75] Inventors: Fabio Broussard, Bergamo; Carlo Busetto, Milan, both of Italy

[73] Assignee: Enichem Synthesis S.p.A., Palermo, Italy

[21] Appl. No.: 846,936

[22] Filed: Mar. 6, 1992

[30] Foreign Application Priority Data

Mar. 7, 1991 [IT] Italy .................. 000594 A/91

[51] Int. Cl.$^5$ .................. C08K 5/3437; C08K 5/18
[52] U.S. Cl. .................. 524/87; 252/403; 524/89; 524/252; 524/255; 524/257; 524/258; 524/291; 524/222; 546/102; 546/174; 564/134; 564/170; 564/179
[58] Field of Search .................. 252/403; 524/87, 89, 524/252, 257, 258, 255, 291, 222; 564/134, 170, 179; 546/102, 174

[56] References Cited

U.S. PATENT DOCUMENTS

| | | | |
|---|---|---|---|
| 3,338,833 | 8/1967 | Spivack et al. | 524/222 |
| 3,554,959 | 1/1971 | Hammersley et al. | 524/255 |
| 3,677,965 | 7/1972 | Dexter et al. | 524/252 |
| 3,703,552 | 11/1972 | Spacht | 564/179 |
| 3,787,355 | 1/1974 | Linhart et al. | 252/403 |
| 3,984,460 | 10/1976 | Spivack | 564/179 |
| 4,822,839 | 4/1989 | Paisner | 524/255 |
| 4,918,124 | 4/1990 | Eichenauer et al. | 524/291 |
| 5,102,939 | 4/1992 | Eichenauer et al. | 524/291 |
| 5,120,792 | 6/1992 | Gatto | 524/222 |

FOREIGN PATENT DOCUMENTS

| | | |
|---|---|---|
| 0002860 | 7/1979 | European Pat. Off. . |
| 0032586 | 7/1981 | European Pat. Off. . |
| 0224788 | 6/1987 | European Pat. Off. . |
| 0225510 | 6/1987 | European Pat. Off. . |
| 0271235 | 6/1988 | European Pat. Off. . |
| 0309285 | 3/1989 | European Pat. Off. . |
| 0319771 | 6/1989 | European Pat. Off. . |

OTHER PUBLICATIONS

J. Lerchora et al.: J. Polymer Science: Symposium No. 57, 249–253 (1976).
J. Pospisil: Plasty a Kaucuk, 23, No. 9, 259 (1986).
K. B. Piotrovskii & K. Yu. Salnis—*Auxiliary Substances for Polymeric Materials*, R. J. Moseley, ed. pp. 11, 12, 17, 19 & 20 (1967).

Primary Examiner—Veronica P. Hoke
Attorney, Agent, or Firm—Oblon, Spivak, McClelland, Maier & Neustadt

[57] ABSTRACT

Stabilizing compositions for organic polymers, composed of mixtures of at least one liquid phenolic antioxidant and at least one aminic antioxidant, subjected to thermal treatment, are characterized by their stabilizing capacity which is considerably higher than that of either single components or of corresponding untreated mixtures.

These stabilizing compositions can be used in all field where the single components of the mixtures are generally used and, preferably, in the stabilization of organic polymers normally subject to deterioration due to oxidation processes.

5 Claims, 2 Drawing Sheets

STABILIZING COMPOSITIONS FOR ORGANIC POLYMERS

The present invention relates to stabilizing compositions having an improved effect, obtained by the thermal treatment of mixtures of phenolic antioxidants with aminic antioxidants.

The use of phenolic antioxidants based on sterically hindered phenols in the stabilization of organic materials partially subject to oxidative deterioration has been known for some time.

In particular, it is well-known (U.S. Pat. No. 3,330,859) that, sterically hindered phenols having the general formula

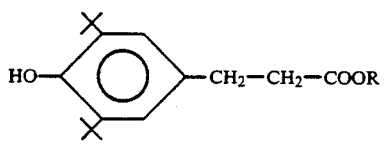

where R is an alkyl radical having from 6 to 20 carbon atoms, are stabilizers against the oxidation of a wide range of polymeric materials among which, the (co)-polymers of vinyl chloride, polyolefins such as polyethylene, polypropylene, polybutene, polyurethanes, polyalcohols, polyesters etc. Other materials to which phenolic antioxidants can be added are lubricating oils of the polyester type (for example pentaerythritoltetracapronate), vegetable and mineral oils.

It is also well-known that secondary aromatic amines of the type

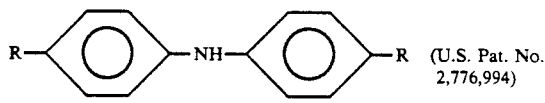

(U.S. Pat. No. 2,776,994)

and, among these, preferably those where $R = C_8H_{17}$, or heterocyclic amines of the type

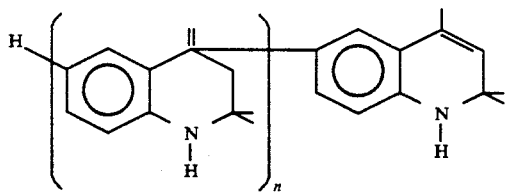

deriving from the condensation of aniline with acetone (J. Voigt; "Die Stabilisierung der Kunststoffe gegen Licht und Waerme" (1986); page 313), or the condensation product of diphenylamine with acetone (as above; page 292), basically composed of 5,5-dimethylacridane, or paraphenylenediamine N,N'-disubstituted (as above; pages 282–284), are excellent antioxidants for vulcanized and non-vulcanized rubbers, polythenes, polycaprolactams, polyurethanes, etc.

These amines actually have an antioxidizing activity which is higher than that of the esters of the above-mentioned hydroxybenzenepropanoic acid.

However, because of the from yellow to brown colouring of the aminic antioxidants, their use is limited to the stabilization of polymers whose colour is not a specific characteristic. When the two types of antioxidants, phenolic and aminic respectively, are used together, their protective effect on the polymeric substrate is either the same or lower than that of the aminic antioxidant alone.

It has now been unexpectedly found that the same antioxidizing mixtures, phenolic and aminic respectively, if subjected to prolonged heat and at suitable temperatures, have a protective activity with respect to the polymeric substrates in which they have been inserted which is from 2 to 5 times higher than that of the above-mentioned mixtures of the known art.

The present invention consequently relates to stabilizing compositions obtained by thermally treating mixtures of antioxidants composed of at least one phenolic antioxidant selected from the alkyl esters of 4-hydroxy-3,5-ditertbutyl-benzene propanic acid having the general formula I

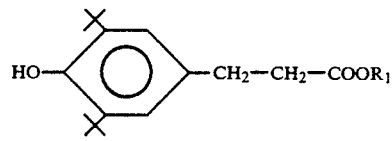

where $R_1$ is a hydrocarbon radical having from 4 to 20 carbon atoms, with at least one aminic antioxidant selected from those corresponding to one of the following general formulae:

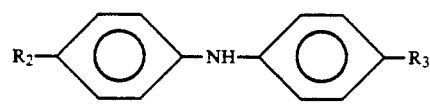

wherein $R_2$ is hydrogen, or a hydrocarbon radical with a number of carbon atoms of between 4 and 12, and $R_3$ is a hydrocarbon radical containing from 1 to 12 carbon atoms; the condensation product of aniline with acetone mainly composed of:

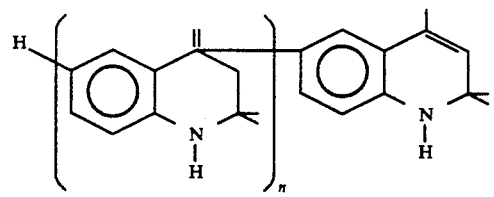

where n is an integer ranging from 1 to 10;

the condensation product of diphenylamine with acetone mainly containing

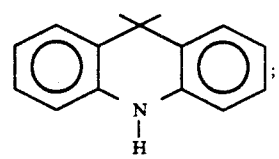

or

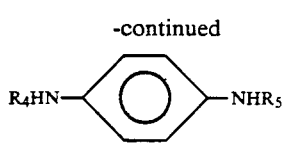

wherein $R_4$ is an alkyl radical containing from 1 to 6 carbon atoms, and $R_5$ may be alkl or phenyl.

The thermal treatment mentioned above consists of heating the mixtures at a temperature ranging from 50° to 150° C., for a period of 0.3 to 6 hours.

The mixtures are preferably treated at temperatures of between 100° and 110° C. over a period of 3 hours.

The sterically hindered phenolic stabilizer used is preferably composed of a mixture of $C_{14}-C_{15}$ esters of benzene propanoic-3,5-bis-(1,1-dimethylethyl)-4-hydroxy acid (formula I, with $R_1$ $C_{14}-C_{15}$ hydrocarbon radical).

As $R_1$ is a mixture of iso $C_{14}-C_{15}$ alcohols, the product is a high boiling light yellow liquid (usually pure esters of the acid are produced in solid form at room temperature).

The validity of the new stabilizing system obtained by prolonged heat treatment of the phenolic antioxidant with aminic antioxidants II and/or III and/or IV, was demonstrated on an unstabilized polyol of Dow Chemical.

In order to verify the stabilizing activity of the compositions of the present patent application and in particular demonstrate the synergetic effect of the thermally treated mixtures of antioxidants in preventing the absorption of oxygen in the polymeric system based on a polyol, a differential thermal analysis was carried out to determine the time necessary to induce the oxidation reaction of the system.

The stabilizer was added at levels of 750–1000 and 1500 ppm.

The measurement of the induction time of oxygen absorption was carried out on a polyol at a temperature of 140° C. under an oxygen flow. The greater the induction time of oxygen absorption, the better will be the stabilizing system used.

A demonstration of the improved stabilizing capacity of the thermally treated mixtures was obtained by observing the induction time of oxygen absorption of the polyol to which the antioxidizing mixture, prepared separately by heating at 100°–110° C. for several hours, had been added, compared with the induction time of the polyol containing the same stabilizers in the mixture but added separately to the polyol.

It was surprisingly discovered that the induction times of oxygen absorption were more than doubled with respect to those observed in the case of the mixtures which had not been thermally treated, as is shown in the examples at the end of the description and in the enclosed tables.

The ratios used between the phenolic and aminic antioxidants in the preparation of the thermally treated mixture may vary to any extent but were suitably chosen to obtain a final product in the form of a transparent liquid without any insoluble substances at room temperature.

The ratios used between the phenolic and aminic antioxidant vary from 10:1 to 10:10.

Preferred mixtures have a ratio by weight between the phenolic and aminic antioxidants of 10:3.

The final product is liquid at room temperature.

This is an enormous advantage with respect to the industrial technique used at present in that the stabilization of the polyol generally requires the addition of either a single solid stabilizer or two consecutive solid stabilizers such as BHT and an alkylate diphenylamine, with the consequent difficulties and prolonged periods of time necessary for a double operation.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

The examples which follow provide an illustration of the present invention but do not limit it in any way.

EXAMPLE 1

1.1 Preparation of PHENOLIC AOX (AOX Ib)

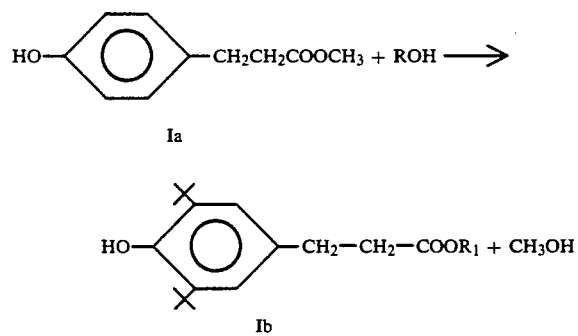

$[R = C_{14}-C_{15}]$ 613 g (2.1 moles) of compound Ia, 436 g (2.0 moles) of a mixture of alcohols $C_{14}-C_{15}$, 2 g of a catalyst normally used in transesterification reactions are charged into a 2 liter 4-neck flask, equipped with a stirrer, thermometer and condenser with a collecting flask.

The mass is subjected to the maximum vacuum of the water pump (20–30 mmHg) and is heated to melting point and to a higher temperature of 160°–165° C. There is a considerable release of methanol which can be controlled by reducing the heat. After two hours the development of methanol is reduced and the temperature is slowly brought up to 170° C. and kept at such for 5 hours.

At this stage, the mass is cooled and the vacuum brought to a few mmHg with the meohanical pump and 40 g of excess compound (Ia) are distilled with a small amount of the unreacted alcohols.

The final conditions were: 210° C. in the boiler, 160° C. in the head, vacuum 0.5 mmHg.

The residue in the boiler is cooled to 60° C., atmospheric pressure is re-established and the product (AOX Ib) is discharged.

940 g of a transparent pale yellow liquid product are obtained, having the following characteristics:

| | |
|---|---|
| density at 25° C.: | 0.937 |

-continued

| Heoppler viscosity at 30° C.: | about 220 cps |
| --- | --- |
| acidity number: | 0.5 |
| volatile products (2 hour at 105° C.): | <0.5% |

1.2 Preparation of the mixture 10:3 or phenolic AOX Ib with aminic AOX (2,2,4-trimethvl-1,2-dihydroquinoline homopolymer)

100 g of AOX Ib are charged into a reactor and heated to 100° C. 30 g of chips of aminic antioxidant (hereafter referred to as ANOX HB) are added, in small portions, under stirring.

The dissolution of the ANOX HB in the ester is not immediate and requires several minutes. It is difficult to determine the duration of the dissolution because the mass becomes extremely dark as the ANOX HB dissolves. The mixture is kept at a temperature of 100° C. under stirring for 3 hours.

The mass is then cooled to 50° C., transferred to a container and left to cool to room temperature. 130 g of an extremely viscous transparent brown liquid product are obtained.

1.3 Test of the stabilizing activity on a polyol of the mixture prepared under point 1.2 by means of differential thermal analysis The oxidation kinetics of the polyol, stabilized with mixtures of different additives, were carried out by means of differential thermal analysis at 140° C.

Figure 2:
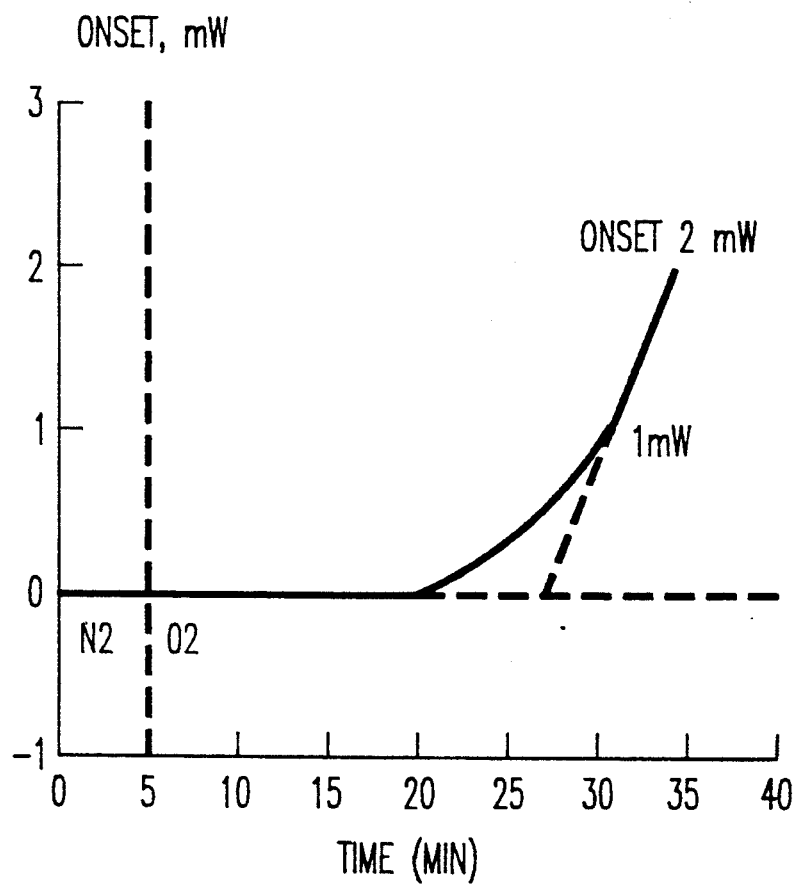
FIG. 2 indicates the amount of heat developed as a function of time.

The analyzed systems were brought under nitrogen within 5 minutes to the analysis temperature inside the measuring capsule. With an oxygen flow (7 ml/h), the oxidation kinetics were observed in relation to the development of heat during the process. The induction time was calculated at the point of contact of the tangent vector to the oxidation curve with the time axis at 1 mW as shown in FIG. 2 which indicates the amount of heat developed (expressed as mW; axis of ordinates), as a function of time.

The addition of the polyol was obtained by stirring until the complete dissolution of the products used.

An experimental product supplied by Dow Chemical, without stabilizers, was used as the polyol.

Table 1 shows the induction times in min. of oxygen absorption in the thermo-oxidation of the polyol at 140° C.

TABLE 1

| THERMO-OXIDATION OF POLYOLS AT 140° C. | | |
| --- | --- | --- |
| Antioxidant | Induction time | % of additive |
| polyol as such | 7.8 min. | — |
| AOX Ib | 8.0 min. | 750 ppm |
| ANOX HB | 13.5 min. | 750 ppm |
| mixture of AOX Ib and ANOX HB thermically treated | 32.1 min. | 750 ppm |

EXAMPLE 2

The product Ib described in Example 1 is used as phenolic AOX.

The condensation product of diphenylamine with acetone called ANOX GAMMA (Bozzetto Rubber Chemicals) was used as aminic AOX.

Using the same procedure described in Example 1, the mixture of AOX Ib: ANOX GAMMA was prepared in various ratios by heating the mass to 110° C. for 3 hours.

The synergetic effect of the phenol with the amine which had been mixed and thermally treated beforehand, was demonstrated by means of the following procedure.

Samples of a polyol were prepared and AOX Ib and ANOX GAMMA mixed directly (and separately) were added to the polyol in different ratios: the total concentration of the stabilizing components was 750 ppm by weight.

Samples of a polyol were also prepared to which the thermally treated mixture of AOX Ib and ANOX GAMMA were added in a concentration of 750 ppm by weight.

The measurements of the induction times observed in the various samples are shown respectively in Table 2a, (the additives were mixed directly in the polyol without any thermal pretreatment) and in Table 2b (various mixtures of AOX Ib and ANOX GAMMA after thermal pretreatment).

TABLE 2a

| THERMO-OXIDATION OF POLYOLS AT 140° C. | | | |
| --- | --- | --- | --- |
| ANOX GAMMA % | AOX Ib % | ppm in polyol | induction time (minutes) |
| 0 | 100 | 750 | 7.8 |
| 20 | 80 | 750 | 10.6 |
| 50 | 50 | 750 | 13.5 |
| 87.5 | 12.5 | 750 | 19.0 |
| 100 | 0 | 750 | 20.1 |

(The additives were mixed directly in the polyol without any thermal pre-treatment).

TABLE 2b

| THERMO-OXIDATION OF POLYOLS AT 140° C. | | | |
| --- | --- | --- | --- |
| ANOX GAMMA % | AOX Ib % | ppm in polyol | induction time (minutes) |
| 15 | 85 | 750 | 24.8 |
| 33 | 67 | 750 | 37.5 |
| 37 | 63 | 750 | 45.0 |
| 50 | 50 | 750 | 54.9 |

(AOX Ib and ANOX GAMMA were mixed and heated for 3 hours at 110° C.

Concentrations of Anox Gamma higher than 50% were not studied as the product is no longer liquid at room temperature).

It can be noted that there is no synergetic effect between the 2 additives mixed directly and separately in the polyol and that the stabilizing effect is simply the sum of the activities of the two components, in relation to their weight ratios (Table 2a).

However, in the case of the polyol to which the thermally treated mixture has been added (Table 2b), there is a considerable increase in the stabilizing activity (Table 2b).

Figure 1:
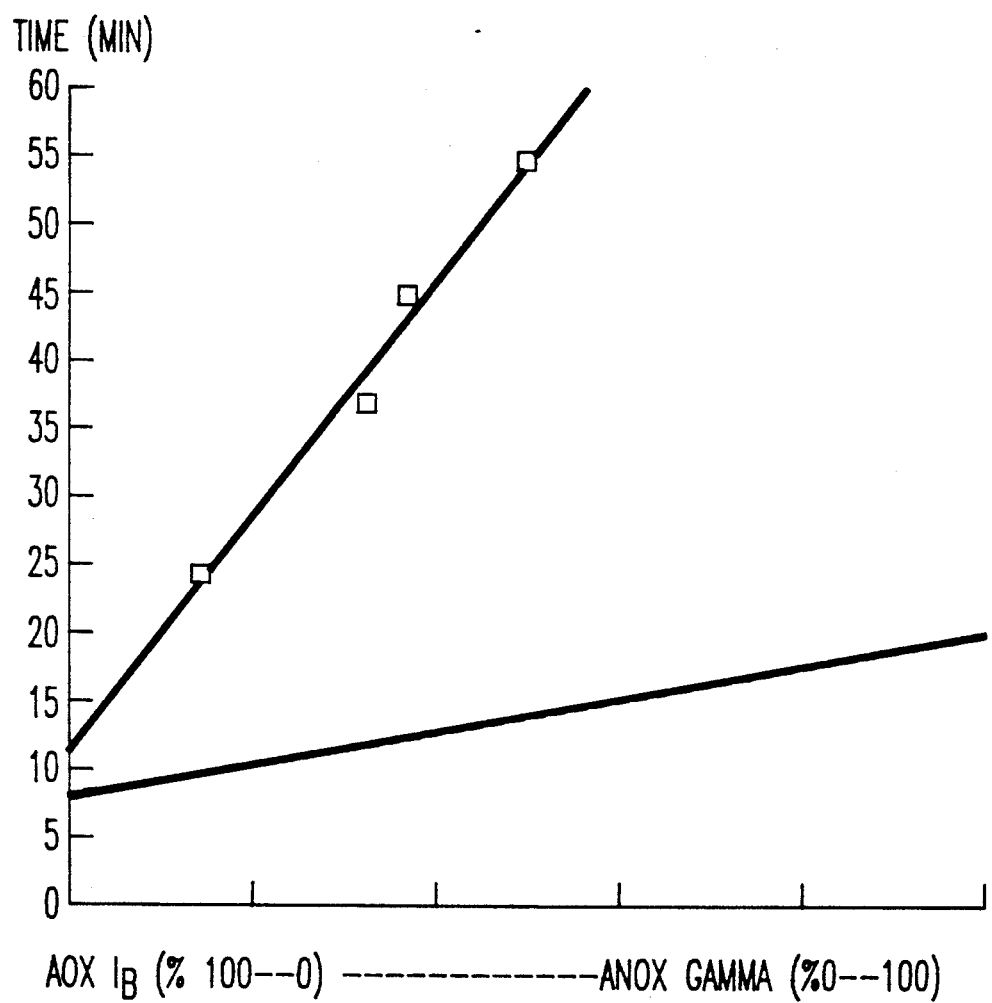
FIG. 1 shows the induction time in relation to the ratio AOX Ib/ANOX GAMMA in the treated and untreated mixtures respectively.

This is also clearly evident in FIG. 1 enclosed which shows the trends of the induction time in relation to the ratio AOX Ib/ANOX GAMMA in their treated (□) and untreated (—) mixtures respectively.

EXAMPLE 3

The product Ib described in Example 1 was used as phenolic AOX.

The diphenylamine dioctylate, i.e. the product called ANOXNS (Bozzetto Rubber Chemicals) was used as aminic AOX.

Using the same procedure described in Example 1, mixtures of AOX Ib:ANOX NS were prepared with different treatment times at 110° C. for 1 hours, 3 hours and 6 hours. The induction times of the tests carried out on the polyol are shown in Table 3.

The mixtures were used in concentrations of 1250 ppm by weight in the polyol.

The best result was obtained with an interaction time of 3 hours.

TABLE 3

| THERMO-OXIDATION OF POLYOLS AT 140° C. | | | | |
|---|---|---|---|---|
| ANOX-NS | AOX Ib | ppm in polyol | interaction time (hrs) | induction time (min.) |
| 3 | 10 | 1250 | 1.0 | 34.3 |
| 3 | 10 | 1250 | 3.0 | 54.7 |
| 3 | 10 | 1250 | 6.0 | 15.8 |

(Stabilizing effect due to the mixture of ANOX NS and AOX Ib, after different interaction times at 110° C.)

EXAMPLE 4

Mixtures of AOX Ib (10 parts) and ANOX GAMMA (3 parts) were prepared as described in Example 2.

The mixtures were heated for 1 hour, 1.5 hours, 3 hours and 6 hours at 100°-110° C.

The measurements were carried out on the polyol to which 900 ppm had been added.

The results are shown in Table 4. Also in this case there is an improved effect due to the prolonged interaction time under heat.

TABLE 4

| THERMO-OXIDATION OF POLYOLS AT 140° C. | | | | |
|---|---|---|---|---|
| ANOX GAMMA | AOX Ib | ppm in polyol | interaction time (hrs) | induction time (min.) |
| 3 | 10 | 900 | 1.0 | 11.7 |
| 3 | 10 | 900 | 1.5 | 13.0 |
| 3 | 10 | 900 | 3.0 | 26.0 |
| 3 | 10 | 900 | 6.0 | 25.4 |

(Stabilizing effect due to the mixture of ANOX GAMMA and AOX Ib, after different interaction times).

We claim:

1. A stabilizing composition, comprising a composition prepared by heating for 0.3 to 6 hours at a temperature range of 50° to 150° C. a mixture of at least one phenolic antioxidant having the formula:

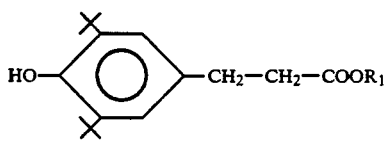

I wherein $R_1$ is a linear or branched hydrocarbon radical containing from 4 to 20 carbon atoms and at least one aminic antioxidant selected from those corresponding to one of the following formulae:

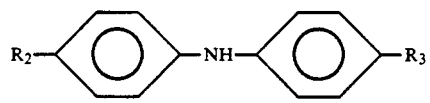

II wherein $R_2$ is hydrogen or a hydrocarbon radical containing from 4 to 20 carbon atoms, and $R_3$ is a hydrocarbon radical containing from 1 to 12 carbon atoms;

the condensation product of aniline with acetone, mainly containing

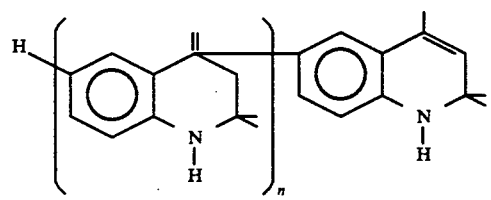

wherein n is an integer ranging from 1 to 10;

the condensation product of dipehnylamine with acetone, mainly containing:

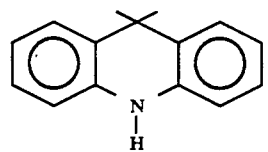

IV or

V wherein $R_4$ is an alkyl radical containing from 1 to 6 carbon atoms; and $R_5$ may be alkyl or phenyl, wherein the phenolic and aminic antioxidants are utilized in a phenolic to aminic weight ratio from 10:1 to 10:10.

2. The stabilizing composition in accordance with claim 1, wherein the mixtures of phenolic antioxidant and aminic antioxidant have been heated to a temperature of between 50° C. and 150° C. for a period ranging from 0.3 to 6 hours.

3. The stabilizing composition in accordance with claims 1 or 2, wherein the mixtures of phenolic antioxidant or aminic antioxidant have been heated to a temperature of between 100° C. and 150° C. for a period of 3 hours.

4. The stabilizing composition in accordance with claim 1, wherein the phenolic antioxidant having general formula I is an ester obtained by esterifying 4-hydroxy-3,5-ditertbutyl-benzene propanoic acid with a mixture of alcohols containing 14–15 carbon atoms.

5. A polymeric composition stabilized by the stabilizing composition of claim 1.

* * * * *